United States Patent [19]
Eliaz et al.

[11] Patent Number: 5,874,093
[45] Date of Patent: Feb. 23, 1999

[54] COSMETIC COMPOSITION CONTAINING MOLECULAR OXYGEN

[76] Inventors: Isaac Eliaz, 260 Waterside Cir., San Rafael, Calif. 94903; Shmuel Gonen, Tnuat Hameri 2, Kiryat-Ono, Israel

[21] Appl. No.: 749,161

[22] Filed: Nov. 15, 1996

[51] Int. Cl.⁶ ...................................................... A61K 7/00
[52] U.S. Cl. .............................. 424/401; 424/45; 514/887
[58] Field of Search ................................ 424/401, 59, 45; 514/80

[56] References Cited

U.S. PATENT DOCUMENTS

| | | | |
|---|---|---|---|
| 4,129,644 | 12/1978 | Kalopissis | 424/59 |
| 4,424,234 | 1/1984 | Alderson | 424/117 |
| 5,472,698 | 12/1995 | Rawlings | 424/401 |
| 5,545,402 | 8/1996 | Watkinson | 424/94.3 |

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

A composition containing a dermatologically acceptable carrier in admixture with molecular oxygen promotes and improves respiratory function of skin cells. The composition may be used in cosmetic compositions.

32 Claims, No Drawings

COSMETIC COMPOSITION CONTAINING MOLECULAR OXYGEN

BACKGROUND OF THE INVENTION

1. Field of the Invention:

The present invention relates to a method for producing a desirable skin cosmetic effect due to the improved metabolism of skin cells, and in particular to the improved respiratory function thereof. The invention relates also to a composition of matter which may be used in this method.

2. Discussion of the Background:

Whatever the action of oxygen contained in the atmosphere on skin cells may be, this can be relevant to the outermost layer of cells only, since there is no evidence that such oxygen penetrates the outer surface of the skin. On the other hand, it is known that making oxygen available to cells of the skin layer generally, has a beneficial effect on the respiratory function of skin cells, which in turn leads to a beneficial cosmetic effect. In the past, this desideratum has been achieved by means of an oxygen-releasing substance added to a vehicle, which penetrates the skin so as to make oxygen available to skin cells besides those in the outermost skin layer. It is believed, however, that this prior art method has a distinct disadvantage, insofar as oxygen released from a chemical compound (i.e., not in the form of molecular oxygen) is likely to be reactive in situ and therefore liable to give rise to possibly irreversible oxidative damage to constituents of the skin cells.

SUMMARY OF THE INVENTION

The present inventors have now discovered that when molecular oxygen is mixed with a suitable carrier, and the mixture is applied to the skin, sufficient oxygen is retained in the mixture so that when the latter penetrates the skin, the molecular oxygen is carried with it and subsequently beneficially affects the metabolism, and in particular the respiration, of skin cells. This discovery may be regarded as a surprising one, since on general grounds it would be expected that the admixed oxygen would be rapidly released to the air, rather than being transmitted through the skin.

It is therefore an object of the invention to provide a method by which molecular oxygen is carried through the outermost layer of skin in order to exert a beneficial effect on the cells of the skin layer generally.

It is also an object of the invention to provide such a method which involves the physical release of oxygen in an admixture, and thereby avoids possible oxidative damage to cell constituents which could be caused by the use of agents which release oxygen by means of a chemical reaction. It is a further object of the invention to provide a method for producing a desirable skin cosmetic effect.

It is yet a further object of the invention to provide a composition of matter which may be used in the method of the invention. Still a further object of the invention is to provide a convenient form in which the composition of the invention may be applied. Other objects of the invention will appear from the description which follows.

The present invention accordingly provides according to one aspect thereof, a composition of matter for producing a desirable skin cosmetic effect due to the improved respiratory function and/or metabolism of skin cells, which comprises a physical admixture of molecular oxygen and a dermatologically acceptable fluorocarbon-free and silicone-free carrier in predetermined proportions, namely about 0.1 to about 4.5 wt. % molecular oxygen with about 95.0 to about 99.9 wt. % of a dermatologically acceptable fluorocarbon-free and silicone-free carrier, which composition is maintained under superatmospheric pressure in a pressurized container. In other aspects of the invention, the carrier need not be fluorocarbon-free and silicone-free, as will be set out in detail in the following description.

From the foregoing summary, it will be apparent that the expression "producing a desirable skin cosmetic effect" includes producing a beneficial effect on the skin and in particular improved respiratory function and/or metabolism of skin cells. Specific examples of a desirable skin cosmetic effect include a reduction in post-acne scarring and a reduction in skin wrinkles relative to skin treated with a control composition or untreated skin.

DETAILED DESCRIPTION OF THE PREFERRED EMBODIMENTS

The dermatologically acceptable fluorocarbon-free and silicone-free carrier used in the composition of the invention is preferably a cosmetically acceptable carrier, and it may be, for example, in the form of a liquid or semisolid, which is non-irritating and does not otherwise adversely affect the skin. It will be appreciated that whereas the use of fluorocarbon and silicone solvents in skin care products is uncommon and to the extent that they are used at all must still be regarded as in the very early experimental stages, the present invention is able to utilize carriers which have been known and used over a period of time. By way of example, any suitable cream or lotion may be utilized; thus, face creams, body lotions, hair creams or lotions, moisture creams, other skin conditioning creams, skin masks, liniments and shaving creams are contemplated for use as carriers in the composition of the invention. As an example of a dermatologically acceptable carrier which is not necessarily cosmetically acceptable, there may be cited petroleum jelly, which may be used as a carrier in accordance with the present invention.

The carrier may contain a dermatologically acceptable α-hydroxy acid. Preferred α-hydroxy acids contain 1–25 carbon atoms. More preferred α-hydroxy acids have the formula HOOC—C(OH)$R^1R^2$ wherein $R^1$ and $R^2$ are, independently, hydrogen or alkyl groups containing $C_{1-10}$ carbon atoms, optionally substituted with an hydroxyl group. Examples of α-hydroxy acids include glycolic acid, lactic acid, 2-hydroxybutyric acid, 2-hydroxycaproic acid, etc. A particularly preferred α-hydroxy acid is glycolic acid. The α-hydroxy acid functions to enhance peeling of dead skin from the skin surfaces (exfoliation) and also aids in penetration of the oxygen into the skin which allows the skin to better regenerate. It also serves as an excellent carrier into the deeper skin layers. The α-hydroxy acid may be present in any amount which is sufficient to perform these functions. Preferably, the α-hydroxy acid will be present in an amount of about 0.25 wt. % to about 20 wt. %, more preferably about 1 wt. % to about 7 wt. %, still more preferably about 1.5 wt. % to about 5 wt. % of the composition of the invention.

It will be appreciated that in general the carrier may comprise at least one member selected from the group consisting of water and organic media such as (for example) ethanol, propanol, isopropanol, glycols (e.g., dipropylene glycol), esters (e.g., isopropyl myristate, isopropyl palmitate and/or diisopropyl adipate) and paraffin oil. In one embodiment, therefore, there may be used an aqueous carrier which comprises, in addition to water, at least one member selected from the group consisting of (for example) ethanol, propanol, isopropanol, glycols (e.g., dipropylene glycol), esters (e.g., isopropyl myristate, isopropyl palmitate and/or diisopropyl adipate) and paraffin oil. In another embodiment of the carrier, added water may be substantially (<10 wt. %) absent, and the carrier will comprise at least one member selected from the group consisting of (for example) ethanol, propanol, isopropanol, glycols (e.g., dipropylene glycol), esters (e.g., isopropyl myristate, isopropyl palmitate and/or diisopropyl adipate) and paraffin oil.

While it is believed that the molecular oxygen, which is a principal ingredient of the admixture of the invention, is unlikely to have a deleterious oxidative effect on either the carrier or the cell constituents, nevertheless, if desired, an antioxidant may be present in the admixture as an added ingredient. Of course, commercially available creams and lotions will often contain antioxidants, and in this case further antioxidant may be optionally added. In the case of a carrier not containing antioxidant this may in any case be added, if desired. Where an antioxidant is used, this may comprise, for example, at least one member selected from the group consisting of BHA (butylated hydroxy anisole), BHT (butylated hydroxy toluene), beta-carotene, propyl gallate and alpha-tocopherol. By way of example only, the carrier may contain from about 0.005 to about 5%, preferably from about 0.1 to about 1%, by weight, of antioxidant. The compositions may also contain e.g., preservatives (including antifungal preservatives); in this context, the parabens, i.e., the alkyl esters (such as the methyl, ethyl, propyl and butyl esters) of p-hydroxybenzoic acid may be utilized.

The admixture of molecular oxygen and carrier is preferably maintained under superatmospheric pressure prior to use, in order to prevent escape of oxygen during storage. Desirably, the admixture is applied to the skin from a pressurized container, such as an aerosol container which contains additionally a propellant. It is preferred that the aerosol container be well shaken before applying the admixture to the skin in accordance with the invention.

It is to be understood that in general, any types of aerosol containers, which are known to those skilled in the art, may be utilized in applying the present invention. Reference may be made, by way of example, to Sanders, Handbook of Aerosol Technology, Van Nostrand Reinhold Company, 2nd Edition 1979, the disclosures of which is incorporated herein by reference. On pages 74–77 of this book there are described the bag-in-can and the piston systems; these systems may be especially useful in applying the present invention insofar as it may be possible to maintain a better constancy of the proportion of oxygen in the composition throughout the life of the aerosol, than when using other aerosol systems. However, this belief should not be construed as detracting from the utility of aerosols generally, in applying the present invention. In the bag-in-can systems, any suitable materials may of course be used for the bag; merely by way of example, Sanders (loc cit) mentions a blend of nylon and polyolefins, but more recently polyethylene, and even aluminum foil have been proposed for this purpose and are acceptable.

In accordance with a particular embodiment, the composition of the invention is generated in the form of a foam, the structure of which maintains an enriched microenvironment of oxygen in contact with the skin. More preferably, a foam stabilizer is incorporated in the composition. Thus according to an embodiment of the invention, there is provided a composition for producing a desirable skin cosmetic effect, which comprises a physical admixture of a predetermined amount of molecular oxygen with a dermatologically acceptable carrier, a propellant, and a foam stabilizer, which composition has been maintained under superatmospheric pressure in a pressurized container from which it is thus applied, the amount of molecular oxygen present in the admixture being not less than 0.1 wt. %, and provided that when the propellant comprises molecular oxygen, then the carrier is a fluorocarbon-free and silicone-free carrier.

This particular embodiment of the invention may also contain an α-hydroxy acid of the type and in the amounts described above.

Examples of foam stabilizers are soaps such as sodium stearate and sodium palmitate, synthetic soaps such as sodium cetyl sulfate, other surface active agents, glycerol, proteins such as gelatin, polymeric foam stabilizers such as methylcellulose and polyvinyl alcohol, other foam stabilizers such as saponins, and mixtures thereof. It will be appreciated that (e.g.) commercially available skin lotions may already contain substances such as surface active agents which may act as foam stabilizers. It is within the competence of a person with skill in this art, to determine whether further foam stabilizer needs to be added to a composition of the invention, what kind of foam stabilizer would be suitable, and the optimum proportion thereof.

The molecular oxygen utilized in accordance with the present invention is preferably substantially pure, although a gas which is enriched in its oxygen content, and which preferably contains at least a major amount of oxygen and trace amounts or at most minor amounts of other harmless gases may also be used. Air, which contains a relatively minor amount of oxygen, is impractical for the present purpose of providing a relatively high concentration in the composition of the invention, although as will be seen from the description below, air may be used for another purpose, i.e., as propellant. Molecular oxygen may be used to provide both the active ingredient of the composition as well as the propellant, except when a fluorocarbon or silicone carrier is utilized.

The propellant may in general be a pressurized gas, preferably one which comprises at least one component selected from the group consisting of carbon dioxide, nitrous oxide, argon, nitrogen and oxygen; e.g., pressurized air may be used. The use of carbon dioxide as propellant is also within the scope of the invention and may be especially advantageous from the point of view of promoting relatively greater penetration of the oxygen through the skin layers. The person skilled in the art is aware that using carbon dioxide in an aqueous medium will create an acidic environment, and will be able to assess the desirability or otherwise of using carbon dioxide as a propellant, taking all relevant factors into consideration.

Alternatively, there may be used a propellant which comprises at least one member selected from the group consisting of propane, butane, isobutane, tichloromonofluoromethane, dichlorodifluoromethane, dichlorotetrafluoroethane, monobromonochlorodifluoromethane, monobromotrifluoromethane, trichlorotrifluoroethane, tetrafluoroethane, octafluorocyclobutane and dimethyl ether. Higher-boiling materials such as (e.g.) pentane and hexane which would be unsuitable for use as propellants on their own, could possibly be used as ingredients of propellant mixtures with lower-boiling components. In view of the flammability of hydrocarbon propellants and of dimethyl ether, and their explosive potentiality when admixed with oxygen, the usual precautions should be exercised when using these materials. Where there is no objection to the use of fluorocarbons (which are usually nonflammable) as propellants, it is particularly preferred that such propellants comprises a mixture of dichloro-difluoromethane and dichlorotetrafluoroethane. Insofar as certain countries, states and local authorities may have enacted legislation prohibiting the use of at least certain of the fluorinated hydrocarbons as propellants due to a belief that they may cause irrevocable damage to the ozone layer, the present disclosure is not intended to invite use of such propellants contrary to this legislation. Indeed, the attention of the skilled person is directed to the alternative propellants which may be used in accordance with the invention.

It will be appreciated that propellants about which concern has been expressed with regard to potential damage to the ozone layer are perhalogenated, i.e., fully halogenated, fluorinated hydrocarbons. Consequently there is at the present time a continuing interest in fluorinated hydrocarbon propellants which are not fully halogenated, such as the following:

1,1,1,2-tetrafluoroethane (134A)—this will probably be stable in all emulsions and aqueous solutions, avoiding possible hydrolysis problems;

1,1-dichloro-2,2,2-trifluoroethane (123) appears to be stable in acid media;

difluoromonochloromethane (22) is until now the most widely used propellant which replaces fully halogenated fluorocarbons, but is relatively unstable in aqueous media and moreover has a high pressure of about 8.8 bar at 21° C.;

1-chloro-1,1-difluoroethane (142B) is relatively unstable in aqueous media at pH above about 10, and also has a tendency to flammability.

Mixtures of (i) 134A with (ii) either 123 or <70% 142B, and optionally (iii) 22, provide a propellant within the invention, preferably with a similar pressure profile to the propellants being currently used. Problems of the relative instability in aqueous media of the newer fluorocarbon propellants may be effectively countered by the presence in these media of epoxides such as propylene oxide, or epoxidized oils such as Epoxol 9-5 (Swift Technical Products), which is stated to be an efficient scavenger of halogen and mineral acids.

A further hazard in the case of ethers such as dimethyl ether, is the possibility of forming explosive peroxides; therefore, such propellants should not be used in the absence of effective peroxide formation inhibitors. As is known in the aerosol art, it is undesirable to use trichloromonofluoromethane as a propellant for aqueous media, because of its liability to hydrolysis; however, this substance may often be suitable for use in the case of substantially non-aqueous carrier media, such as those comprising alcohols and/or paraffin oil.

Many alternatives in the use of pressurized gas propellants will suggest themselves to those skilled in the art. In one alternative, already indicated above, an aerosol canister containing a skin treatment composition (including foam stabilizer) may be pressurized with oxygen, which thus acts as the active ingredient as well as propellant. Alternatively, an optimum predetermined amount of oxygen may be added so as to be substantially completely dissolved in the composition, and the canister may then be pressurized with e.g. compressed air or carbon dioxide. In another alternative, a reusable high pressure vessel containing the composition components including a foam stabilizer and oxygen may be pressurized with gas added from an attachable reservoir such as a cartridge; in this case, pressurized propellant gas may be released into the vessel (by for example piercing a valve in the neck of a cartridge) when the reservoir is (e.g.) screwed in, as is known for example, in the case of domestic devices for making carbonated water where the carbon dioxide is injected into the contents of a pressure bottle in this manner.

In these additional embodiments also, an α-hydroxy acid may be added in the amounts and for the purposes described above.

As regards the proportions of the ingredients of the admixture, it is preferred that this comprises in general about 0.1 to about 4.5 wt. % molecular oxygen and about 95.5 to about 99.9 wt. % carrier. When using an aerosol or other pressure vessel, the mixture of ingredients therein may comprise, e.g., about 0.1 to about 4.5 wt. % molecular oxygen, about 1.0 to about 25.0 wt. % propellant, about 72.0 to about 97.75 wt. % carrier, and about 0.05 to about 1.0 wt. % foam stabilizer; and preferably about 1.25 to about 1.35 wt. % molecular oxygen, about 9.0 to about 11.0 wt. % propellant, about 86.65 to about 89.6 wt. % carrier, and about 0.05 to about 1.0 wt. % foam stabilizer.

The invention will now be illustrated by the following examples in which the commercially available body lotion specified incorporates foam stabilizer.

EXAMPLE I

In accordance with substantially known industrial procedures, a standard aerosol can of approximately 20 cc capacity was filled with an admixture of 90 g commercially available body lotion, a propellant which contained dichlorodifluoromethane (4 g) and dichlorotetrafluoroethane (6 g), and 1.3 g molecular oxygen. The initial pressure of the can prior to addition of oxygen was about 40 psig at 70° F.

The contents of the aerosol can were well shaken and the admixture contained therein, which was propelled therefrom in the form of a stabilized foam, was applied to newborn hairless mice on the dorsal side. On each mouse, the area of application was divided into two sections, to one of which was applied the admixture in accordance with the invention, and to the other of which was applied the same body lotion without admixed oxygen. After two hours, the mice were sacrificed, the skin was peeled and mitochondria were isolated according to the method described by T. P. Singer in "Methods of Biochemical Analysis" (Ed., D. Glick) 22:123–75 (1974). The activity of two of the main components of the respiratory chain, succinic oxidase and NADH oxidase were assayed according to Singer's method. The results are described in the following table:

|  | Enzyme specific activity | |
| --- | --- | --- |
| Body lotion | succinic oxidase | NADH oxidase |
| control | 131.5 | 64.8 |
| + oxygen | 182.4 | 103.0 |

The data indicate that due to the presence of oxygen in the lotion, the rate of activity of essential components of the respiratory chain of the cells is significantly elevated, thus demonstrating an enhancement of the general respiratory metabolism of the cells. It may be noted that the control experiment related to a foam generated in the presence of air, but was very much less effective than the experiment generated with molecular oxygen in accordance with the invention.

EXAMPLE II

The following composition may be used in place of the admixture of Example I, and gives similar results, namely 95 g. commercially available body lotion, a propellant which comprised butane (3.75 g.) and propane (1.25 g.), and 1.3 g. molecular oxygen. The initial pressure of the can prior to addition of oxygen was about 40 p.s.i.g. at 70° F.

EXAMPLE III

The following composition may be used in place of the admixture of Example II, and gives similar results, namely 95 g. commercially available body lotion, a propellant which comprised butane (3.33 g.), isobutane (0.5 g.) and propane (1.17 g.), and 1.3 g. molecular oxygen. The initial pressure of the can prior to addition of oxygen was about 40 p.s.i.g. at 70° F.

EXAMPLE IV

An aerosol can which contained 100 g. commercially available body lotion was pressurized with oxygen only, to a pressure of 9 atm. gauge at 70° F. In this instance, the oxygen served the dual function of dissolving as active ingredient in the body lotion, as well as a propellant. In place of an aerosol can, there may be utilized a re-usable pressure vessel to which the oxygen may be added by an attachable reservoir.

EXAMPLE V

A mixture of commercially available body lotion (100 g.) with molecular oxygen (1.3 g.) in an aerosol container under slight superatmospheric pressure is subsequently pressurized to 9 atm. gauge at 70° F. using as propellant nitrogen, compressed air or carbon dioxide. In place of an aerosol can, there may be utilized a re-usable pressure vessel to which the propellant may be added by an attachable reservoir.

EXAMPLE VI

A mixture of commercially available body lotion (100 g.) with molecular oxygen (1.3 g.) and glycolic acid (2.5 wt. %) in an aerosol containing under slightly superatmospheric pressure is subsequently pressurized to 9 atm. gauge at 70° F. using as propellant nitrogen, compressed air or carbon dioxide. In place of an aerosol can, there may be utilized a re-usable pusher vessel to which the propellant may be added by an attachable reservoir.

EXAMPLE VII

The therapeutic effect of the molecular oxygen-containing composition of the invention for treatment of post-acne scarring was evaluated with four female volunteers having post-acne scarring on their faces. A molecular oxygen-containing cream of the invention was applied daily for 3–10 months. All four women had significant improvement in their condition. In one of the four subjects, the scarring almost completely disappeared.

The table below shows the therapeutic effect of the composition of the invention on the four subjects tested.

| Subject # | Age | Baseline | Application time (months) | Results |
|---|---|---|---|---|
| 1 | 28 | deep scars | 3 | Marked improvement |
| 2 | 24 | deep scars | 8 | Almost completely disappeared |
| 3 | 42 | deep scars | 6 | Marked improvement |
| 4 | 27 | deep scars | 10 | Marked improvement |

All four subjects responded well to the treatment. Three of four subjects exhibited marked improvement, and one of the subjects had almost complete disappearance of post-acne scars. These results show that the composition of the invention is an effective topical treatment for post-acne scaring.

While the invention has been particularly described and exemplified with respect to certain embodiments, it will be apparent to those skilled in the art that modifications and variations may be made in different aspects of the invention, as for example, in the selection of the carrier, in the proportions of the ingredients, and in the nature and composition of the propellant, where used. Accordingly, the invention is not to be construed as limited to such embodiments, rather it will be defined only in accordance with the claims which follow.

What is claimed as new and desired to be secured by Letters Patent by the United States is:

1. A composition of matter for improving at least one of skin cell metabolism and skin cell respiratory function which comprises:

a physical admixture of about 0.1 to about 4.5 wt. % molecular oxygen and about 95.5 to about 99.9 wt. % of a dermatologically acceptable fluorocarbon-free and silicone-free carrier wherein said composition is maintained under superatmospheric pressure in a pressurized container.

2. The composition of claim 1, wherein said carrier is a cosmetically acceptable carrier.

3. The composition of claim 1, wherein said carrier comprises at least one member selected from the group consisting of water, ethanol, propanol, isopropanol, glycols, esters and paraffin oil.

4. The composition of claim 3, wherein said carrier comprises water and at least one member selected from the group consisting of ethanol, propanol, isopropanol, glycols, esters and paraffin oil.

5. The composition of claim 3, wherein said carrier comprises at least one member selected from the group consisting of ethanol, propanol, isopropanol, glycols, esters and paraffin oil, in the substantial absence of added water.

6. The composition of claim 1, further comprising an antioxidant.

7. The composition of claim 6, wherein said antioxidant comprises at least one member selected from the group consisting of butylated hydroxyanisole, butylated hydroxytoluene, beta-carotene, propyl gallate and alpha-tocopherol.

8. A composition of matter for improving at least one of skin cell metabolism and skin cell respiratory function, which comprises a physical admixture of a predetermined quantity of molecular oxygen with a dermatologically acceptable carrier, a propellant, and a foam stabilizer, which composition is maintained under superatmospheric pressure in a pressurized container, the amount of molecular oxygen present in said admixture being not less than 0.1 wt. %, and provided that when said propellant comprises molecular oxygen, then said carrier is a fluorocarbon-free and silicone-free carrier.

9. The composition of claim 8, wherein said propellant comprises at least one component selected from the group consisting of carbon dioxide, nitrous oxide, argon, nitrogen and oxygen.

10. The composition of claim 9, wherein said propellant comprises air.

11. A composition of matter for improving at least one of skin cell metabolism and skin cell respiratory function, which comprises a physical admixture of a predetermined quantity of molecular oxygen with a dermatologically acceptable carrier, a propellant, and a foam stabilizer, which composition is maintained under superatmospheric pressure in a pressurized container, the amount of molecular oxygen present in said admixture being not less than 0.1 wt. %, and wherein the propellant comprises at least one member selected from the group consisting of propane, butane, isobutane, trichloromonofluoromethane, dichlorodifluoromethane, difluoromonochloromethane, difluoromonochloromethane, dichlorotetrafluoroethane, dichlorotrifluoroethane, monobromomonochlorodifluoromethane, monobromotrifluoromethane, trichlorotrifluoroethane, tetrafluoroethane, octafluorocyclobutane and dimethyl ether.

12. The composition of claim 11, wherein said propellant comprises at least two members selected from the group consisting of propane, butane and isobutane.

13. The composition of claim 11, wherein said propellant comprises at least one member selected from the group consisting of 1,1,1,2-tetrafluoroethane, 1,1-dichloro-2,2,2-trifluoroethane, difluoromonochloromethane and 1-chloro-1,1-difluoroethane.

14. The composition of claim 13, further comprising a scavenger for halogen and/or mineral acids.

15. The composition of claim 11, wherein said propellant comprises trichloromonofluoromethane, and said carrier is a substantially non-aqueous carrier.

16. The composition of claim 11, wherein said propellant comprises dimethyl ether and further comprises a peroxide formation inhibitor.

17. A composition of matter for improving at least one of skin cell metabolism and skin cell respiratory function, which comprises a physical admixture of a predetermined quantity of molecular oxygen with a dermatologically acceptable carrier, a propellant, and a foam stabilizer, which composition has been maintained under superatmospheric pressure in a pressurized container, the amount of molecular oxygen present in said admixture being not less than 0.1 wt. %, and wherein the propellant comprises at least one component selected from the group consisting of carbon dioxide, nitrous oxide, argon and nitrogen.

18. The composition according to claim 8, wherein said physical admixture comprises about 0.1 to about 4.5 wt. % molecular oxygen, about 1.0 to about 25.0 wt. % propellant, about 72.0 to about 97.75 wt. % carrier and about 0.05 to about 1.0 wt. % foam stabilizer.

19. The composition according to claim 11, wherein said physical admixture comprises about 0.1 to about 4.5 wt. % molecular oxygen, about 1.0 to about 25.0 wt. % propellant, about 72.0 to about 97.75 wt. % carrier and about 0.05 to about 1.0 wt. % foam stabilizer.

20. The composition according to claim 17, wherein said physical admixture comprises about 0.1 to about 4.5 wt. % molecular oxygen, about 1.0 to about 25.0 wt. % propellant, about 72.0 to about 97.75 wt. % carrier and about 0.05 to about 1.0 wt. % foam stabilizer.

21. The composition of claim 1, further comprising about 0.25 wt. % to about 20 wt. % of an α-hydroxy acid.

22. The composition of claim 8, further comprising about 0.25 wt. % to about 20 wt. % of an α-hydroxy acid.

23. The composition of claim 11, further comprising about 0.25 wt. % to about 20 wt. % of an α-hydroxy acid.

24. The composition of claim 17, further comprising about 0.25 wt. % to about 20 wt. % of an α-hydroxy acid.

25. A method of increasing the respiratory metabolism of skin cells, comprising contacting skin cells with the composition of claim 1.

26. A method of increasing the respiratory metabolism of skin cells, comprising contacting skin cells with the composition of claim 8.

27. A method of increasing the respiratory metabolism of skin cells, comprising contacting skin cells with the composition of claim 11.

28. A method of increasing the respiratory metabolism of skin cells, comprising contacting skin cells with the composition of claim 17.

29. A method of treating post-acne scarring, comprising topically administering to a patient in need thereof a scar reducing effective amount of the composition of claim 1.

30. A method of treating post-acne scarring, comprising topically administering to a patient in need thereof an effective amount of the composition of claim 8.

31. A method of treating post-acne scarring, comprising topically administering to a patient in need thereof an effective amount of the composition of claim 11.

32. A method of treating post-acne scarring, comprising topically administering to a patient in need thereof an effective amount of the composition of claim 17.

* * * * *